(12) United States Patent
Tornier

(10) Patent No.: US 8,048,114 B2
(45) Date of Patent: Nov. 1, 2011

(54) DEVICE AND UNIT FOR THE POSTERIOR DYNAMIC GUIDANCE OF THE SPINE AND TREATMENT SYSTEM COMPRISING SUCH A DEVICE

(75) Inventor: Alain Tornier, Saint Ismier (FR)

(73) Assignee: Clariance, Dainville (FR)

( * ) Notice: Subject to any disclaimer, the term of this patent is extended or adjusted under 35 U.S.C. 154(b) by 678 days.

(21) Appl. No.: 12/155,115

(22) Filed: May 29, 2008

(65) Prior Publication Data

US 2008/0300631 A1    Dec. 4, 2008

Related U.S. Application Data

(60) Provisional application No. 60/924,804, filed on May 31, 2007.

(30) Foreign Application Priority Data

May 31, 2007    (FR) ...................................... 07 03881

(51) Int. Cl.
*A61B 17/70*    (2006.01)

(52) U.S. Cl. ...................................................... 606/246

(58) Field of Classification Search .................. 606/246, 606/247, 250, 251, 252, 257, 258, 259, 279, 606/300, 301; 623/17.11–17.16
See application file for complete search history.

(56) References Cited

U.S. PATENT DOCUMENTS

| 7,318,825 | B2 * | 1/2008 | Butler et al. ..................... 606/71 |
| 7,766,940 | B2 * | 8/2010 | Kwak et al. ................... 606/247 |
| 7,862,586 | B2 * | 1/2011 | Malek ............................ 606/246 |
| 2002/0183757 | A1 | 12/2002 | Michelson |
| 2004/0087951 | A1 * | 5/2004 | Khalili ............................ 606/69 |

FOREIGN PATENT DOCUMENTS

| WO | WO 03/094699 | 11/2003 |
| WO | WO 2005/062900 | 7/2005 |

\* cited by examiner

*Primary Examiner* — Pedro Philogene
(74) *Attorney, Agent, or Firm* — Young & Thompson

(57) ABSTRACT

A guidance device including two vertebral units adapted to be fixed to the posterior side of two adjacent vertebrae of the spine and wherein the two units have substantially spherical complementary articulation surfaces which, when the units are fixed to the vertebrae, extend overall on the posterior side of the vertebrae and slide against one another about a center point located in the intervertebral space that separates the vertebrae, and wherein the device also includes a mechanical element to limit an amplitude of the relative sliding of the articulation surfaces.

15 Claims, 12 Drawing Sheets

DEVICE AND UNIT FOR THE POSTERIOR DYNAMIC GUIDANCE OF THE SPINE AND TREATMENT SYSTEM COMPRISING SUCH A DEVICE

BACKGROUND OF THE INVENTION

1. Field of the Invention

The present invention relates to a device for the posterior dynamic guidance of the spine, which is intended to be implanted along the posterior side of the spinal column in order to guide the movements of two adjacent vertebrae one relative to the other, by reproducing an intervertebral articulated joint. The invention also relates to a unit comprising at least two of these devices, and to a spinal treatment system comprising such a device.

The invention thus relates to the treatment of degenerative spine disease or spinal trauma, particularly in the dorsolumbar region of the spinal column, but also in the region of the cervical spine.

2. Brief Description of the Related Art

To treat intervertebral instability one known first option is to fuse two adjacent vertebrae, which amounts to depriving these two vertebrae of any freedom of relative movement. Completely rigid fixators are therefore implanted fixedly along the spine to permanently immobilize the joint between the two vertebrae that are to be fused. This arthrodesis intervention does, however, lead to degeneration of the adjacent disks which then often require later treatment.

Another known treatment option is to operate at an earlier stage than an arthrodesis would require and is aimed at implanting a posterior dynamic guidance device as proposed for example in WO-A-03/094699. For this purpose, the device comprises, first, bone anchoring screws for anchoring into the posterior side of two adjacent vertebrae and, second, elastic elements connecting these screws. These elastic elements are, in theory, intended to relieve the load on the intervertebral disk and correct any excessive pressure on the articulation surfaces between this disk and the vertebrae. By comparison with an arthrodesis treatment, this type of device offers the patient greater comfort because it allows the mobility of the spine to be maintained. However, in practice, it proves tricky to use: it is difficult to determine the elasticity of the connecting elements because this elasticity has to be tailored to each patient according to his surgical requirement and build. In addition, ultimately there is a risk that the elastic behavior of these elastic elements may change. Imperfect control of the parameters relating to the elasticity of these elements means that the desired spinal mobility cannot be guaranteed and this may lead to mediocre guidance or even to instability in the intervertebral gap and aggravate the lesions that the intervention was supposed to be treating.

SUMMARY OF THE INVENTION

It is an object of the present invention to propose a device for the posterior dynamic guidance of the spine, that more faithfully reproduces the anatomical movement of the vertebrae by guiding these in a manner that is effective reliable and stable over time.

To this end, the subject of the invention is a device for posterior dynamic guidance of the spine, comprising two vertebral units respectively designed to be fixed to the posterior side of two adjacent vertebrae of the spine, wherein the two vertebral units respectively define substantially spherical complementary articulation surfaces which, when the two vertebral units are fixed to the vertebrae, extend overall on the posterior side of the vertebrae and slide against one another, being centered at one and the same geometric point located in the intervertebral space that separates the two vertebrae, and wherein the device comprises dynamic limitation mechanical means designed to limit the amplitude of the relative sliding of the articulation surfaces.

The idea underlying the invention is that of guiding the relative movements of the two vertebrae respectively equipped with the vertebral units, not by way of elastic elements connecting these units, but by way of the direct cooperation of these units, at their concentric spherical articulation surface(s) positioned on the posterior side of the vertebrae. In this way, the dynamic movement imposed on the vertebrae by the collaboration of these articulation surfaces is predetermined in a manner that is precise, reliable and stable over time. This dynamic movement can be likened to that of a pseudo-ball joint centered in the intervertebral space, preferably in the central region of this space, which causes the vertebrae to exhibit a dynamic articulation behavior similar to that of their normal anatomical behavior, both in terms of flexion-extension and in terms of twisting and lateral bending. Furthermore, collaboration between these articulation surfaces relieves the load on the disk that lies between the two vertebrae: the dimensions, particularly the vertical dimension, of the intervertebral space are actually maintained, in that this space is not reduced because the device according to the invention bears most, if not all, of the stresses associated with spinal movements. In other words, by virtue of the dynamic action of the device, the intervertebral disk is not compressed and therefore retains its normal anatomical mobility.

The invention also incorporates control over the amplitude of the relative movements of the vertebrae thus guided by the vertebral units, thanks to the dynamic limitation means. These means are effective and precise because of their mechanical nature. In addition, they have a two-fold practical effect: with respect to the vertebrae, they prevent these from departing from a preset range of freedom of movement, which is advantageously tailored to the build of the patient and/or to the condition being treated and, with respect to the vertebral units of the device, they are able to keep the articulation surfaces in contact with one another over substantial proportions of these surfaces, via which the mechanical stresses are effectively transferred between the vertebral units.

What is more, the device according to the invention proves to be particularly easy to implant: the mobility internal to the device lies essentially, if not exclusively, at the articulation surfaces defined by the vertebral units, of which the anchoring positions in the posterior side of the vertebrae to be treated are chosen and fixed by the surgeon. Furthermore, because these articulation surfaces extend posteriorly with respect to the spine, the actions involved in surgical implantation are concentrated behind the spine.

According to other advantageous features of the device according to the invention, considered in isolation or in any technically feasible combination:

- each vertebral unit comprises a single cup delimiting the entire corresponding articulation surface in the form of a cap which, when the vertebral unit is fixed to its associated vertebra extends on each side of the saggital plane of this vertebra;
- each unit comprises a pair of two separate cups distant from one another in a substantially medio-lateral direction and each delimiting part, preferably half, of the corresponding articulation surfaces;

the single cup or each cup of the pair of each vertebral unit has a concave face facing toward the posterior side of the associated vertebra when the vertebral unit is fixed to this vertebra;

each vertebral unit comprises two pads for fixing to the posterior face of the vertebra associated with this unit, which pads are distant from one another in a substantially medio-lateral direction and are both connected to the single cup or to each cup of the pair by respective ears each forming a peripheral extension of the cup with the same curvature;

each unit comprises two pads for bone fixing to the posterior face of the vertebra associated with this unit, which pads are distant from one another in a substantially medio-lateral direction and are joined together by a reinforcing beam both equipped with the pads at each of its longitudinal ends and connected rigidly to the single cup or to each cup of said pair;

the dynamic limitation means comprise, firstly, a peg dynamically connected to a first of the two vertebral units and at least partially extending from the or one of the articulation surfaces defined by this first vertebral unit toward the or one of the articulation surfaces defined by the second of the two vertebral units and, secondly, an orifice that houses the peg with clearance for travel, this orifice being formed by the second vertebral unit and opening onto the articulation surface defined by this second vertebral unit;

the orifice passes right through the second vertebral unit in a substantially anterior-posterior direction and thus opens onto an opposite surface of the second vertebral unit to its articulation surface, and the peg extends into this orifice, fixedly connecting a first assembly piece positioned on the same side as the opposite surface to a second assembly piece positioned on the opposite side of the first vertebral unit to its articulation surface;

the opposite surface of the second vertebral unit is spherical such as to be concentric with the articulation surfaces, and the first assembly piece delimits a spherical surface that complements the opposite surface and is designed to slide against this opposite surface during relative sliding of the articulation surfaces;

the device further comprises an elastic shock-absorbing means interposed between the two vertebral units.

Another subject of the invention is a unit for the posterior dynamic guidance of the spine, wherein the unit comprises at least two guide devices as defined hereinabove, and wherein a first vertebral unit of one of the devices and a first vertebral unit of the other or of one of the other devices are partially common, particularly as far as their bone attachment is concerned, and are designed to be fixed to one and the same intermediate vertebra while the second vertebral units of the two devices are respectively designed to be fixed to an inferior vertebra and a superior vertebra which are adjacent to the intermediate vertebra.

The guide unit according to the invention can be used to treat three or more adjacent vertebrae.

A further subject of the invention is a system for treating the spine, wherein the system comprises a device for posterior dynamic guidance of the spine as defined hereinabove and a means of temporarily immobilizing this device which is designed to be connected removably to the vertebral units and therefore prevent relative sliding of the articulation surfaces.

This immobilizing means makes the guide device easier to implant by temporarily neutralizing the internal mobility of this device, particularly while the vertebral units are being fixed to the vertebrae. The surgeon can then precisely determine the position at which to anchor the vertebral units, particularly in such a way as to locate the geometric center of the articulation surfaces appropriately, preferably in the central region of the intervertebral space. Once these vertebral units have been fixed to the vertebrae, the immobilizing means is disengaged by the surgeon and the intervention of implanting the device can be completed.

According to one advantageous feature of this system, the immobilizing means comprises two pins housed respectively in complementary notches formed in the vertebral units, the two notches of each vertebral unit being both aligned in a direction passing through the central region of the or one of the articulation surfaces defined by this vertebral unit and situated on each side of this central region in this direction.

BRIEF DESCRIPTION OF THE DRAWINGS

The invention will be better understood from reading the description which will follow, which is given solely by way of example and with reference to the attached drawings, in which.

DESCRIPTION OF THE PREFERRED EMBODIMENTS

Figure 1:
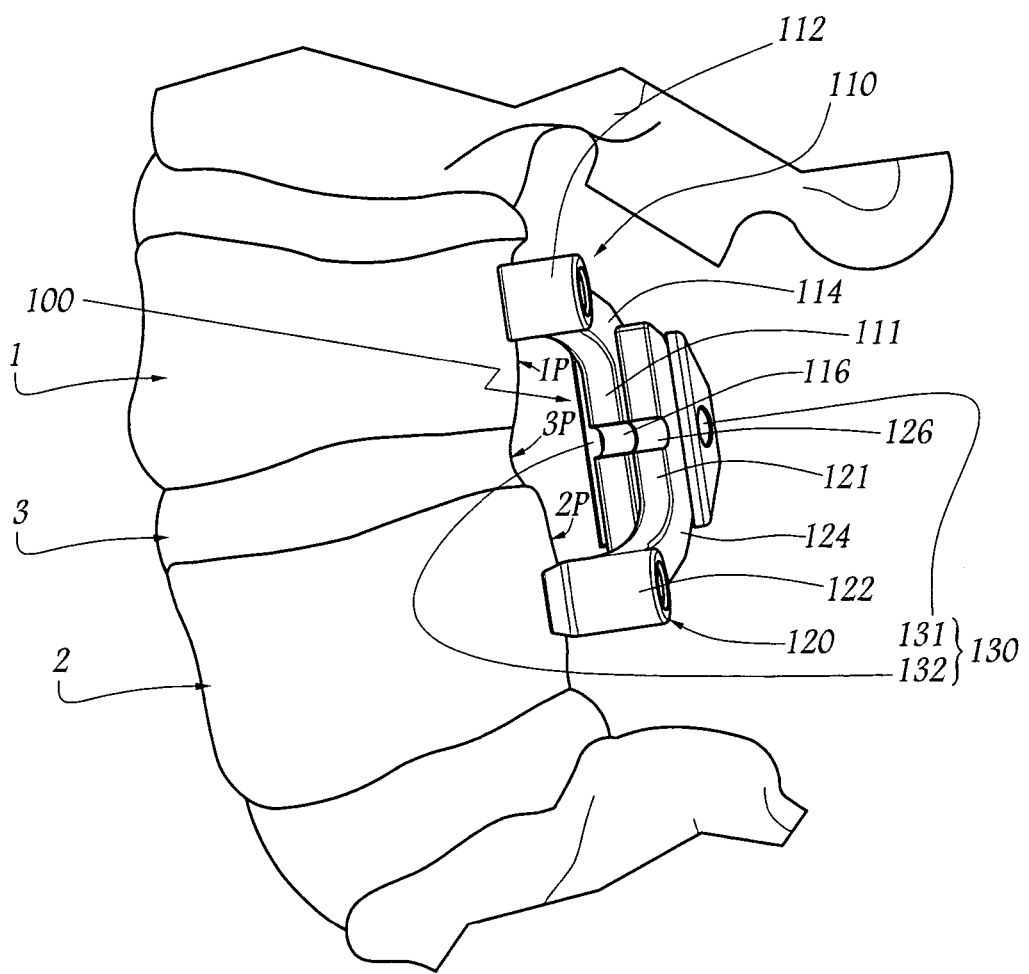
FIGS. 1 and 2 are lateral and posterior elevations, respectively, of a device according to the invention, depicted schematically in a configuration for implantation in a spine.
Figure 2:
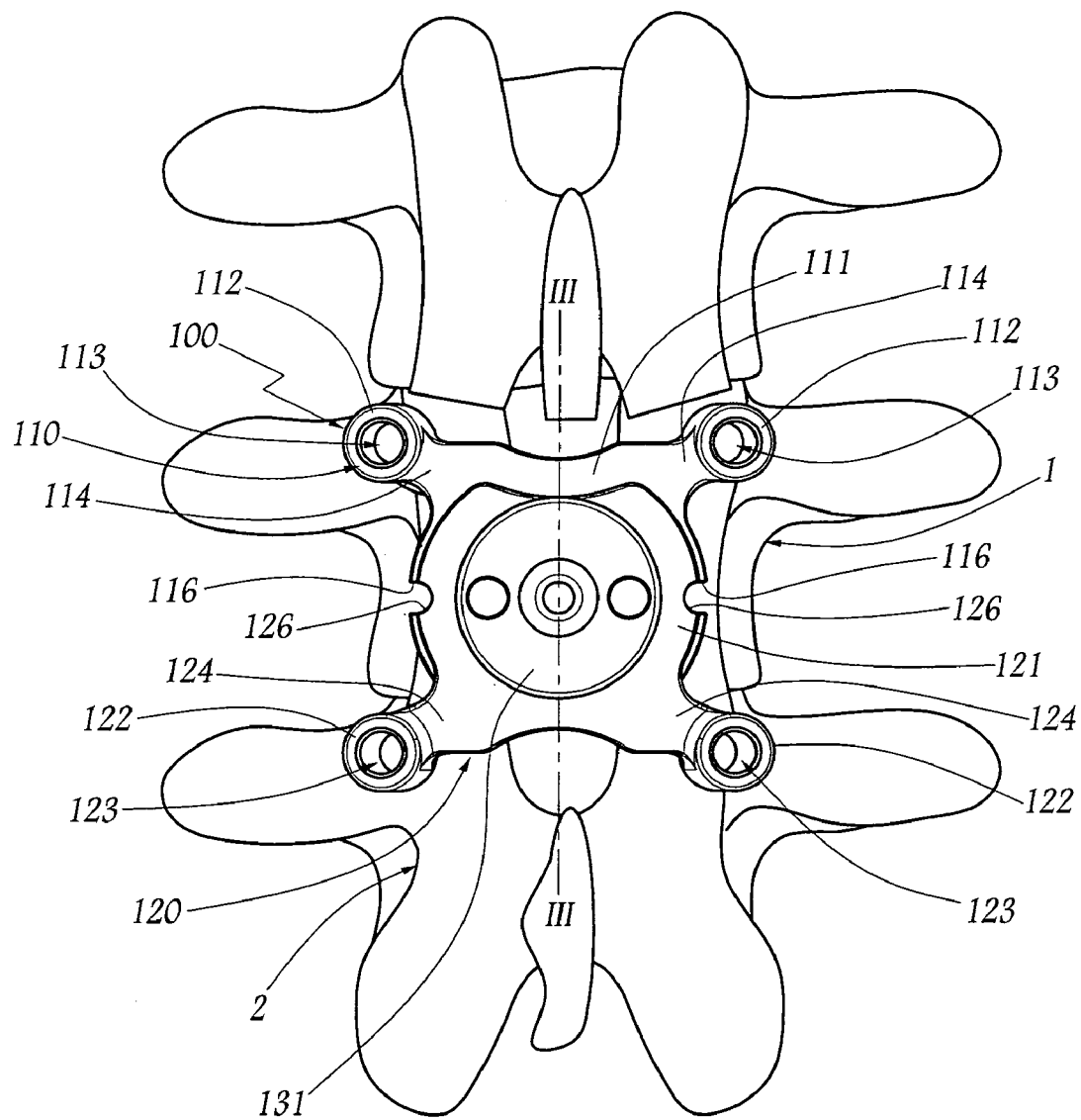
Figure 3:
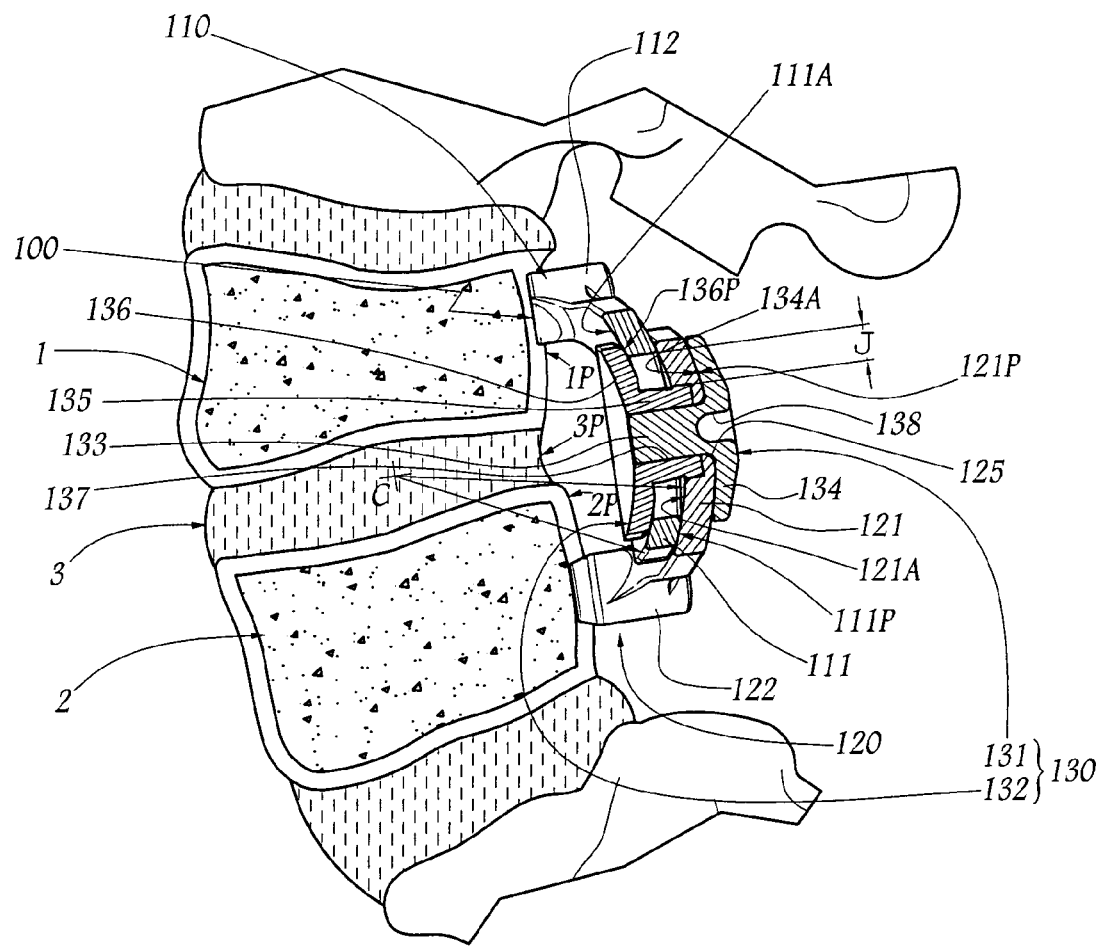
FIG. 3 is a section on III-III of FIG. 2.

FIGS. 1 to 3 depict two adjacent vertebrae 1 and 2 of the lumbar spine of a human patient. These vertebrae are separated from one another by an intervertebral disk 3. For convenience, the remainder of the description is oriented with respect to these vertebrae in their anatomical position, that is to say that the terms "posterior" or "rear", "anterior" or "front", "right", "left", "superior", "inferior", etc. relate to the spine of the patient standing up.

FIGS. 1 to 5 depict a device 100 for guiding the vertebrae 1 and 2, which is implanted on the posterior side of the vertebrae and is capable of providing a posterior articulated mechanical joint between these vertebrae, while at the same time maintaining the intervertebral space that vertically separates these vertebrae and which is occupied by the disk 3. The device 100 comprises a superior vertebral unit 110 implanted on the vertebra 1 and an inferior vertebral unit 120 implanted on the vertebra 2.

Each vertebral unit 110, 120, comprises a rigid cup 111, 121, for example made of metal or ceramic. The two cups 111 and 121 generally extend on the posterior side of the vertebrae 1 and 2, being nested one inside the other, the cup 111 being positioned forward and inside the cup 121. The two cups thus have their respective concave face facing towards the posterior side of the vertebrae.

The cup 111 delimits, firstly, a concave anterior surface 111A extending from the top downward, successively directly opposite the respective posterior faces 1P, 3P and 2P of the vertebra 1 of the disk 3 and of the vertebra 2, and secondly, a convex posterior surface 111P. The cup 121 for its part delimits, firstly, a concave anterior surface 121A that complements the surface 111P and, secondly, a convex posterior surface 121P. As is clearly visible in FIG. 3, the surfaces 111A, 111P, 121A and 121P are spherical surfaces respectively corresponding to portions of a sphere in the form of spherical caps, all centered on one and the same geometric point C located in the intervertebral space occupied by the disk 3.

When viewed in posterior elevation, as in FIG. 2, the cups 111 and 121 generally extend over most of the medio-lateral dimension of the vertebrae 1 and 2. Thus, the spherical surfaces 111A and 111P, 121A and 121P of these cups extend on each side of the saggital plane and their associated vertebra 1, 2, this plane corresponding to the line III-III in FIG. 2.

Each cup 111, 121 is equipped with two bone fastening pads 112, 122, in the form of tubes internally delimiting through-orifices 113, 123 opening onto the posterior face 1P, 2P of their associated vertebra 1, 2. Each orifice 113, 123 is designed to accept an anchoring screw, not depicted, that anchors the screw in the boney material that the vertebra 1, 2 constitutes, in order to fasten the unit 110, 120 to its associated vertebra. The two pads 112 are respectively situated at superior peripheral regions of the cup 111, while the two pads 122 are respectively situated in inferior peripheral regions of the cup 121. Advantageously, the two pads 112 and 122 respectively are aligned in a medio-lateral direction on each side of the saggital plane of the vertebrae 1 and 2 respectively so that their respective orifices 113, 123 open onto the pedicles of the vertebra, which are posterior regions of the vertebra where the boney material is of a good anchoring quality.

For this purpose, each pad 112, 122 is respectively secured to its cup 111, 121 by an ear 114, 124 rigidly connecting a portion of the exterior periphery of the cup to the exterior face of the tube that forms the pad. Each ear 114, 124 extends in the spherical continuation of the cup 111, 121, that is to say that the anterior and posterior faces of each ear respectively form part of the spherical envelopes defined by the anterior surface 111A, 121A and by the posterior surface 111P, 121P of the cup 111, 121. The tubes forming the pads 112 and 122 are transversal with respect to their corresponding ear 114, 124. The ears 114 and 124 thus each correspond to materially continuous peripheral extensions of the cup 111, 121, with the same curvature as the cup, thus making these ears easier to manufacture, particularly by allowing them to be cast and/or machined as one with the cup.

Thus, each unit 110, 120 advantageously defines a vertical plane of symmetry which passes through the point C and which coincides substantially with the saggital plane of the vertebra 1,2.

The pads 122 have an anterior-posterior dimension greater than that of the pads 121 so that when the device 100 is in the implantation configuration, that is to say when the vertebral units 110 and 120 are fixed to the vertebrae 1 and 2 by insertion and tightening of bone anchoring screws in the pads 112 and 122, the cup 121 covers the cup 111 with the surfaces 111P and 121A pressed directly against one another.

Thus, when the device 100 is in the implantation configuration, the surfaces 111P and 121A collaborate with one another on the posterior side of the spine, through having complementing shapes, being capable of sliding one against the other, centered on the point C. These surfaces 111P and 121A therefore constitute articulation surfaces for the articulation between the vertebral units 110 and 120, relative sliding of these surfaces corresponding to rotational movements centered on C, so that the dynamic connection between these two units can be likened to that of a ball joint connection with center C. In point of fact, the relative sliding of the two surfaces 111P and 121A can be had in all directions of space, as long as contact between these surfaces is maintained. Thus, insofar as the articulation center C is positioned in the interdiskal space, particularly in the central region of this space, the dynamics imposed on the vertebral units 110 and 120 by the collaboration of the surfaces 111P and 121A causes the vertebrae 1 and 2 to exhibit relative dynamic behavior that is identical or, at the very least, similar, to their normal anatomical behavior both in flexion-extension and in twisting and left/right bending. In particular, the posterior spherical collaboration of the cups 111 and 121 is designed to maintain the vertical spacing of the vertebrae 1 and 2, preventing the disk 3 from becoming stressed and thus allowing this disk to retain its natural mobility. The cap shape of the articulation surfaces 111A and 121P guarantees that the dynamic guidance of the units 110 and 120 and therefore of the vertebrae 1 and 2 will be suitably uniform in all directions in which the spine is called upon to move.

In order to limit the amplitude of the sliding between the articulation surfaces 111P and 121A, the device 100 incorporates corresponding dynamic limitation means 130. In the example considered here, these means 130 comprise two separate parts 131 and 132 connected on each side of the cups 111 and 121 in an anterior-posterior direction. The posterior piece 131 comprises a cylindrical stub 133 equipped, at its rear longitudinal end, with a projecting peripheral rim 134. The anterior surface 134A of the rim 134 complements the surface 121P so that these surfaces press directly against one another when the pieces 131 and 132 are assembled. To this end, the cup 121 has, passing right through it in an anterior-posterior direction, a through-orifice 125 of a cross section tailored to that of the stub 133, as clearly visible in FIG. 3.

The anterior piece 132 comprises a cylindrical peg 135 equipped, at its front longitudinal end, with a projecting peripheral rim 136. The posterior surface 136P of the rim 136 complements the surface 111A so that these surfaces can press directly against one another. The peg 135 internally delimits a longitudinal hole 137 that accepts and immobilizes the front part of the stub 133. In particular, the hole 137 and the stub 133 may be tapped and threaded respectively with complementary screw threads, so that the piece 131 can be secured rigidly to the piece 132 by screwing them together. To make this screwing-together easier, the posterior surface 134P of the rim 134 is advantageously provided with a socket for turning the piece 131 on itself, the socket here being configured as two diametrically opposed recesses 139. More generally, the stub 133 and the hole 137 are designed to collaborate so that the pieces 131 and 132 can be securely assembled with one another.

The peg 135 has, on the one hand, sufficient anterior-posterior length that it can both pass right through the cup 111, via a through-orifice 115 in this cup, and reach the surface 121A and, on the other hand, a cross section that is non-circular but of oblong shape. By making the anterior mouth of the orifice 125 have an oblong cross section tailored to that of the peg 135, fitting the posterior end of this peg in this mouth when the pieces 131 and 132 are being assembled prevents the piece 132 and the cup 121 from being able to rotate relative to one another. Because the cup 121 is therefore also immobilized by the cup 111 toward the front and by the rim 134 toward the rear, the cup 121 is thus fixedly connected to the pieces 131 and 132.

Unlike the orifice 125, the orifice 115 has a cross section which is not tailored to that of the peg 135. Rather, the cross section of this orifice has dimensions greater than those of the external profile of the peg 135, in all directions of the plane transversal to this peg. In the exemplary embodiment considered here, the orifice 115 has a cross section of oblong shape, substantially homothetic with that of the exterior profile of the cross section of the peg 135, with the respective major axes of these two oblong shapes running generally in a vertical direction while their respective minor axis runs in a substantially medio-lateral direction. Thus, when the pieces 131 and 132 are assembled with one another, the peg 135 extends through the orifice 115, and there is a not-insignificant amount of clearance, both vertically and medio-laterally, between the peg 135 and the wall of the cup 111 delimiting the orifice 115, as visible in the case of the vertical clearance denoted J in FIG. 3. It will be appreciated that during relative sliding of the articulation surfaces 111P and 121A, the peg 115 changes position within the orifice 115 until, if appropriate, it butts against a peripheral portion of the wall delimiting this orifice, thus limiting the amplitude of the relative sliding of the cups 111 and 121.

Advantageously, the rim 136 delimits a posterior surface 136P that complements the surface 111A, against which the surface 136P is pressed directly when the pieces 131 and 132 are assembled with one another. Thus, the rims 134 and 136 keep the device 100 in the assembled configuration, that is to say hold the cups 111 and 121 pressed against one another insofar as, when the surfaces 111P and 121A slide against one another, the surfaces 111A and 136P slide against one another accordingly.

Figure 4:
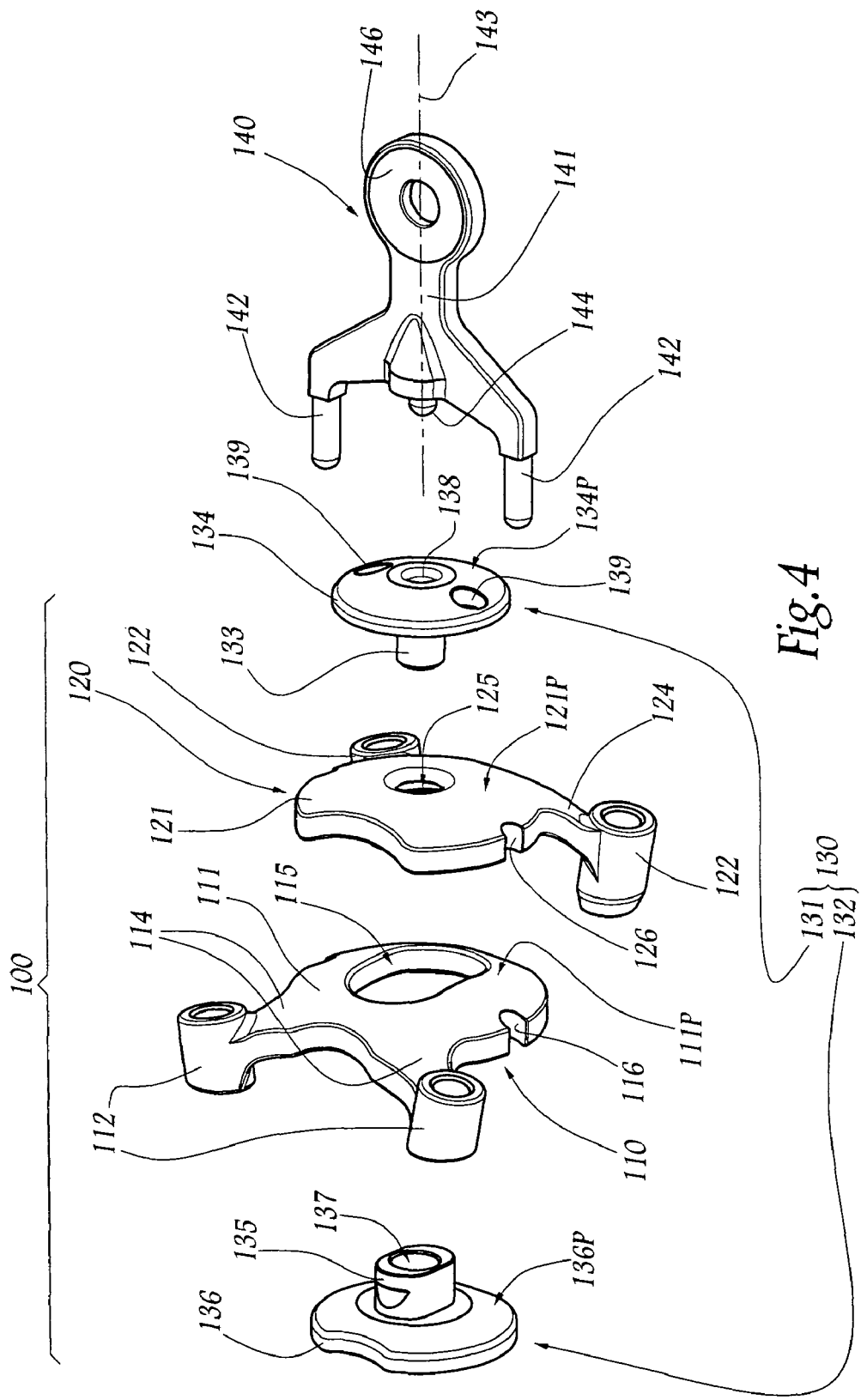
FIG. 4 is an exploded perspective view of a treatment system according to the invention comprising the device of FIGS. 1 to 3.
Figure 5:
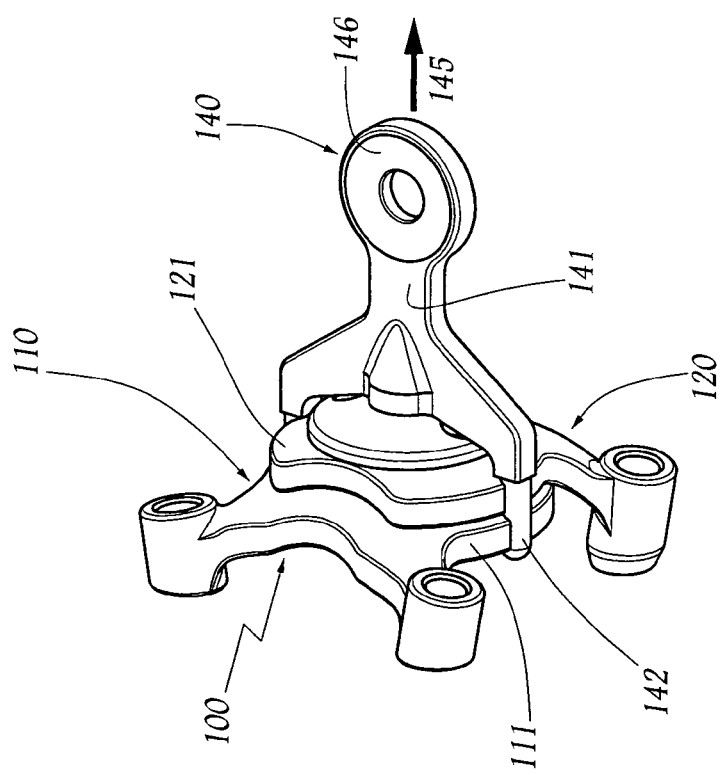
FIG. 5 is a perspective view of the system of FIG. 4 in a configuration for use of this system.

The device 100 is advantageously associated with a fork 140 depicted in FIGS. 4 and 5. This fork comprises an elongate main body 141 equipped, at one of its longitudinal ends with two parallel pins 142 extending parallel to a central longitudinal axis 143 of the body 141 and symmetrically with respect to one another. Each pin 142 is designed to be housed lengthwise in two notches 116 and 126 delimited respectively by the cups 111 and 121. The two notches 116 of the cup 111 are diametrically opposed on the exterior periphery of this cup, and also aligned in a medio-lateral direction. Likewise, the two notches 126 of the cup 121 are diametrically opposed on the exterior periphery of this cup, and likewise aligned in a medio-lateral direction. Thus, the notches 116 and 126 open pairwise one end to the next when the central regions of the cups 111 and 121 are aligned in an anterior-posterior direction, that is to say when the articulation surfaces 111P and 121A are pressed against one another in a centered manner as in FIGS. 1 to 3 and 5. With the cups 111 and 121 in this relative position, the pins 142 can be inserted, from the rear forward, into, successively the notches 126 and 116 and, because the shapes of these pins and those of the notches complement one another, the fork 140 immobilizes the cups with respect to one another as shown in FIG. 5.

Advantageously, the anterior end of the body 141 is equipped, in addition to the two pins 142, with a cylindrical stub 114 centered on the axis 143 and designed to be housed in a complementary manner in an associated recess 138 in the piece 131, opening onto the surface 134P. The fitting of the stub 144 into the recess 138 improves the fitting of the fork 140 in as much as the stub and the recess advantageously exhibit arrangements that allow the stub to clip into the recess, so that disengagement of the fork 140 then requires a corresponding unclipping effort, thus reducing the risks of accidental fork disengagement.

To implant the device 100 on the vertebrae 1 and 2, a surgeon, via initially a posterior route, moves aside the soft tissue of the patient which is situated on the posterior side of the vertebrae. He then resects the spinal processes of the vertebrae 1 and 2 together with, if necessary the inferior part of the spinal process of the vertebra situated just above the vertebra 1 and the superior part of the spinal process of the vertebra situated just below the vertebra 2, as situated just below the vertebra 2, as depicted in FIGS. 1 to 3. In practice, this resection of the spinal process(es) needs to be extensive enough that the device 100 can be brought, from the rear forward, into contact with the posterior faces 1P and 2P of the vertebrae 1 and 2, with the pads 112 and 122 opening directly onto these boney faces so that anchoring screws, not depicted, can be introduced and screwed thereinto via a posterior route.

To do this, the surgeon has the device 100 in an assembled state, that is to say with the units 110 and 120 assembled and held together by the pieces 131 and 132 secured to one another. Furthermore, during placement and attachment of the device 100 along the vertebrae 1 and 2, the fork 140 is used to immobilize the relative movements of the cups 111 and 121, that is to say that the device 100 is handled together with the fork 140 in their assembled configuration shown in FIG. 5. Thus, the surgeon fixes the vertebral units 110 and 120 to the vertebrae 1 and 2 whiles these two units are immobilized, centered, one relative to the other. The precision with which the device 100 can be implanted is thus improved. Furthermore, because the fork 140 neutralizes the internal mobility of the device 100, the surgical operations are far easier for the surgeon to perform because, when fixing the device 100 to the vertebrae 1 and 2, this surgeon does not need to concern himself with the relative positioning of the units 110 and 120.

In practice, if required, the device 100 is implanted under stress in order to relieve the load on the disk 3, that is to say that the units 110 and 120 are fixed to the vertebrae 1 and 2 while the latter are kept separated from one another in a predetermined way by a suitable ancillary device. The amount of separation imposed between the vertebrae can be made equal to that of a normal anatomical separation or may be deliberately larger than this normal separation, depending on the condition being treated. For example, in order to treat a spinal crush problem chiefly affecting the posterior sides of the vertebrae, making the space larger in this way may prove highly beneficial, particularly because it will effectively relieve the pain and discomfort experienced by the patient.

Once the device 100 has been fixed to the vertebrae 1 and 2, the fork 140 is disengaged, by unclipping the stub 144 from the recess 138 and withdrawing the forks 142 from the recesses 116 and 126. To do this, the surgeon pulls the body 141 backward along its axis 143, as indicated by the arrow 145 in FIG. 5, advantageously holding onto a pull tab 146 provided at the opposite end of the body 141 to the end that is equipped with the pins 142.

The device 100 is then in the implantation configuration of FIGS. 1 to 3. The surgeon then closes up the soft tissue posterior to the vertebrae 1 and 2 and the surgical operation is completed. Following implantation, the device permanently maintains its internal mobility associated with the sliding of the articulation surfaces 111P and 121A against one another, within the limit of travel imposed by the means 130.

Figure 6:
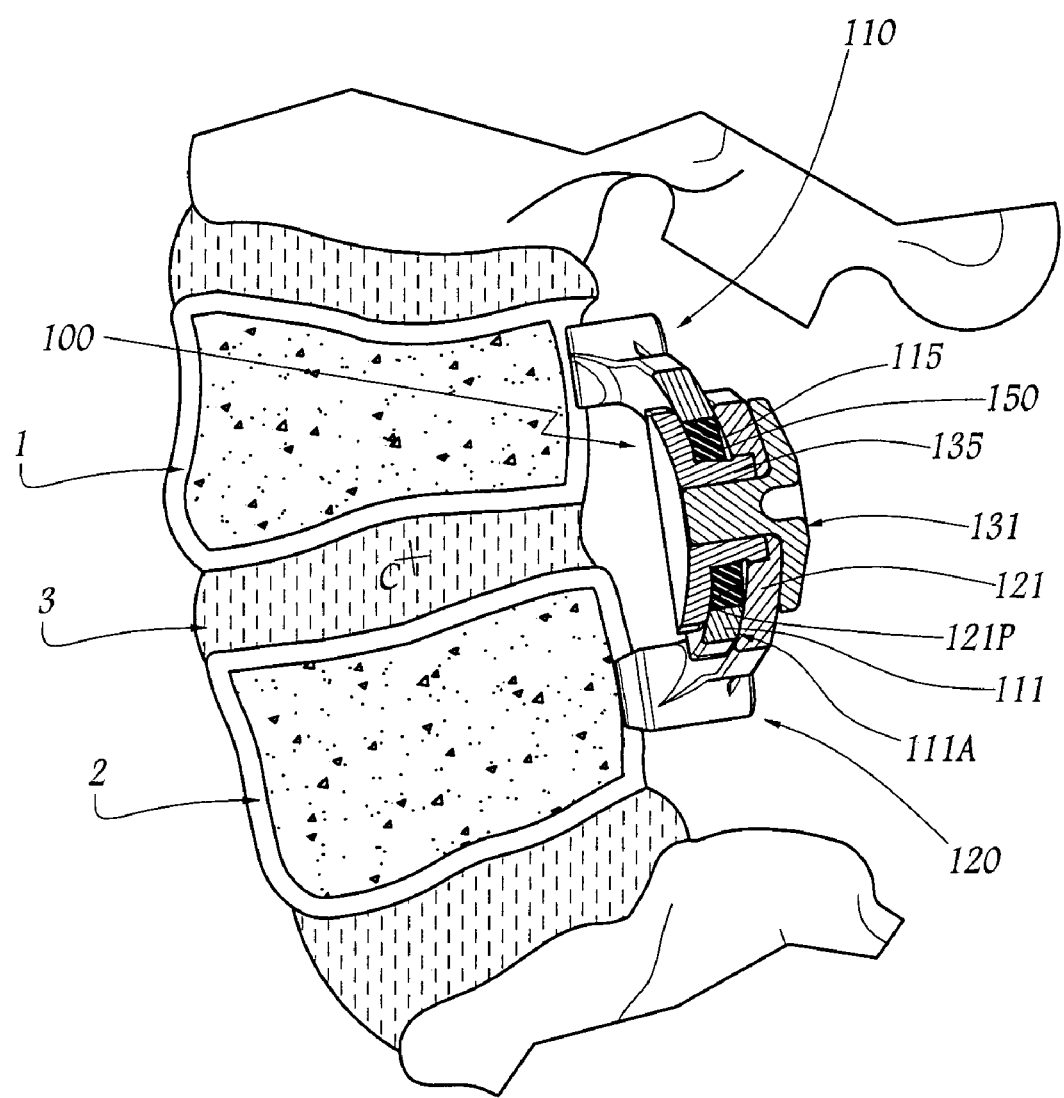
FIG. 6 is a view similar to FIG. 3, illustrating an optional arrangement of the device.

FIG. 6 depicts the device 100 of FIGS. 1 to 5 with an optional arrangement that consists of a washer 150 made of a soft material and occupying the empty space between the peg 135 and the wall of the hole 115, which space is connected with the clearance for relative travel of the cups 111 and 121. This washer 150 is thus interposed, in general radially with respect to the central longitudinal axis of the peg 135, between this peg and the wall of the orifice 115.

In service, when the surface 111P and 121A slide against one another, the washer 150 damps the relative sliding of the cups 111 and 121, preventing the peg 135 from coming into abutment too sharply with the wall of the orifice 115, thus limiting the corresponding discomfort to the patient.

Figure 7:
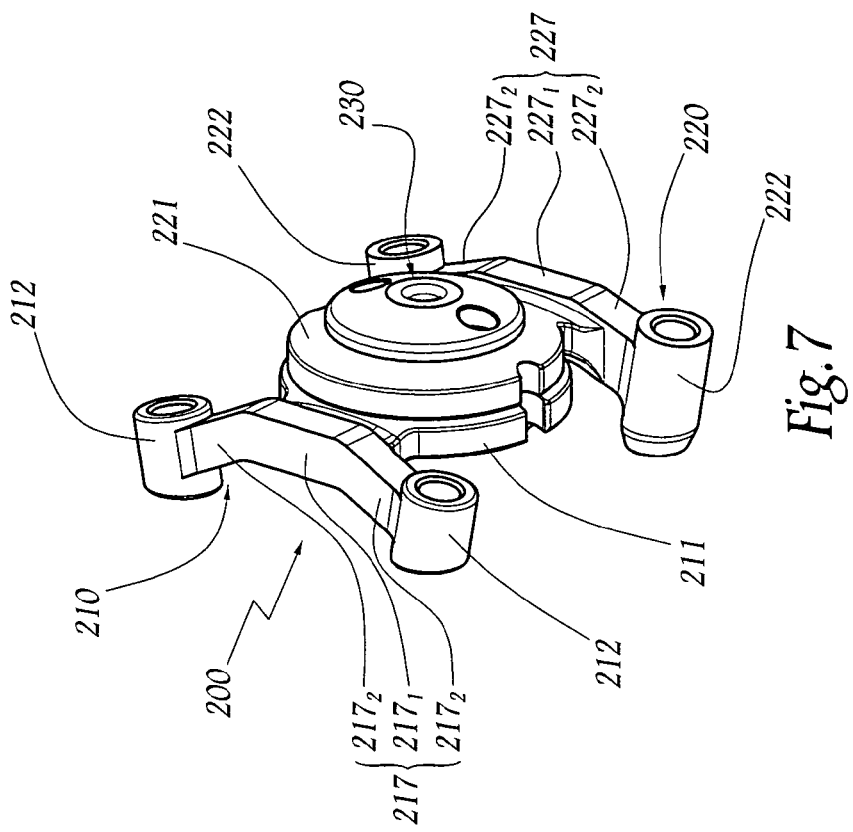
FIG. 7 is a perspective view of an alternative form of the device according to the invention.

FIG. 7 depicts an alternative form 200 of the device 100. The device 200 comprises two vertebral units, a superior one 210 and an inferior one 220, the respective cups 211 and 221 of which are identical to the cups 111 and 121 of the units 110 and 120 of the device 100. The device 200 also comprises dynamic limitation mechanical means 230 identical to the means 130 of the device 100. The device 200 differs from the device 100 in the way in which the rigid connection between each of its cups 211 and 221 and their pair of bone attachment pads 212 and 222 are embodied. Specifically, instead of the ears 114 and 124 provided in the device 100, the device 200 comprises, for each vertebral unit 210, 220, a beam 217, 227. Each beam 217, 227 comprises a main section $217_1$, $227_1$ running lengthwise in a medio-lateral direction and extended at each of its longitudinal ends by a bent-forward end section $217_2$, $227_2$. At their opposite end, the end sections $217_2$, $227_2$ are rigidly connected to the pads 212, 222, while the cup 111, 121 is rigidly connected, over a corresponding portion of its external periphery, to the main section $217_1$, $227_1$.

The beams 217 and 227 are more bulky than the ears 114 and 124 but correspond to a mechanically more robust structure, the beam shape improving the ability to withstand the dynamic stresses transmitted between the cup 211, 221 and the corresponding vertebra 1, 2.

The device 200 is implanted in exactly the same way as the device 100, it being possible in particular to make use of the fork 140.

FIGS. 8 to 11 depict a second embodiment of the device 300 for guiding the vertebrae 1 and 2, of which the dynamic behavior and the effects on these vertebrae are substantially identical to those of the device 100 or 200.

The device 300 comprises, firstly, a superior vertebral unit 310 fixed to the posterior face 1P of the vertebra 1 by two anchoring screws, not depicted, housed in two fixing pads 312 connected rigidly to one another by a beam 317, these pads 312 and the beam 317 having a structure identical to the pads 212 and to the beam 217 of the device 200 and, secondly, an inferior vertebral unit 320 fixed to the face 2P of the vertebra 2 by two anchoring screws, not depicted, housed in two attachment pads 322 rigidly connected to one another by a beam 327, with a structure identical to that of the pads 222 and of the beam 227 of the unit 220 of the device 200.

The device 300 differs from the device 200 in the way in which its units 310 and 320 collaborate with one another in terms of relative sliding. Specifically, rather than having a single cap-shaped cup like the cups 211 and 221 of the device 200, each unit 310, 320 comprises two cups $311_1$ and $311_2$, $321_1$ and $321_2$ in the form of quarters of a sphere. These two cups $311_1$ and $311_2$, $321_1$ and $321_2$ are distant from one another in an anterior-posterior direction so that between them they delimit an empty space extending on each side of the saggital plane of their associated vertebra 1, 2. As is clearly visible in FIGS. 10 and 11, when the device 300 is implanted, a substantial part of the spinal process 1E of the vertebra 1 extends rearward through this empty space, which means that implanting the device 300 entails less resection of spinal process(es) than implanting the devices 100 and 200, although it must be pointed out that localized resections of the spinal processes are still necessary because of the main section $317_1$, $327_1$ of the beam 317 and 327.

The cups $311_1$ and $311_2$, $321_1$ and $321_2$ are respectively rigidly secured to the two end sections $317_2$, $327_2$ of their respective beam 317, 327.

Figure 11:
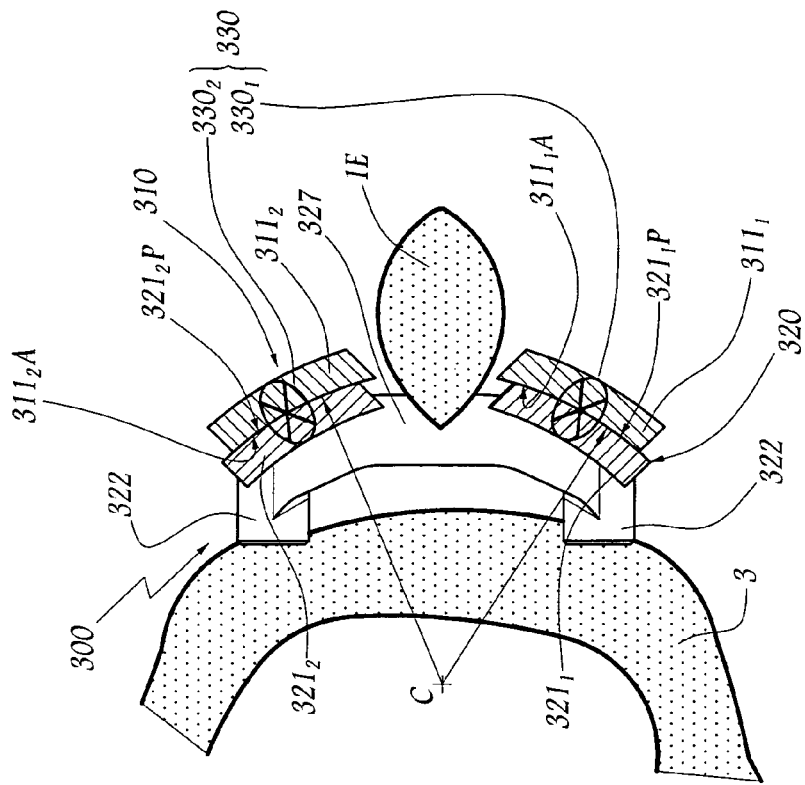
FIG. 11 is a section on XI-XI of FIG. 9.
Figure 8:
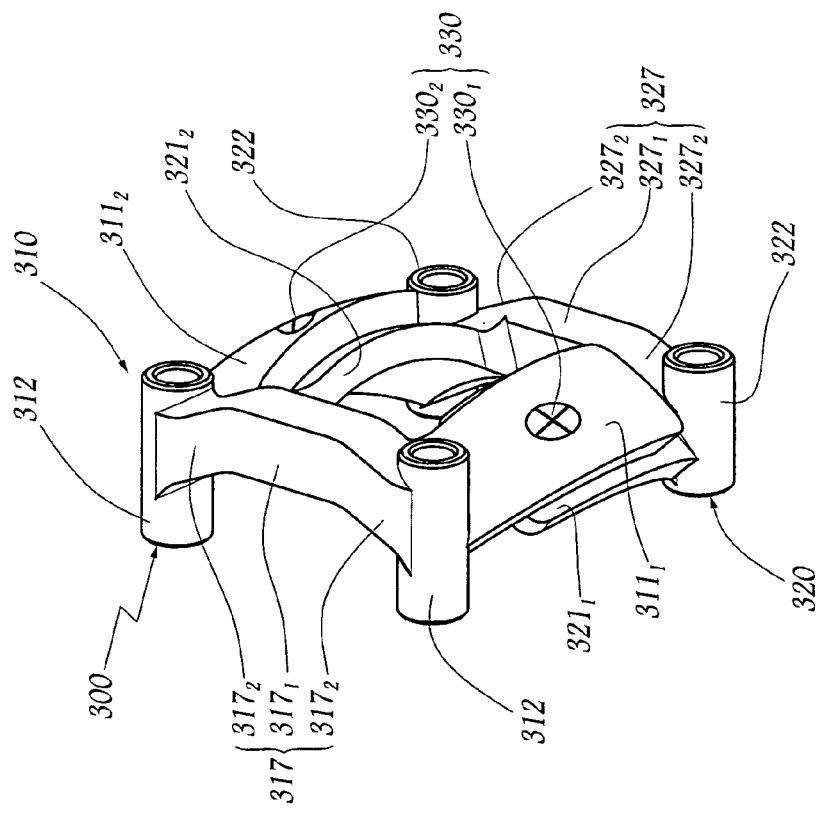
FIG. 8 is a perspective view of a second embodiment of a device according to the invention.
Figure 9:
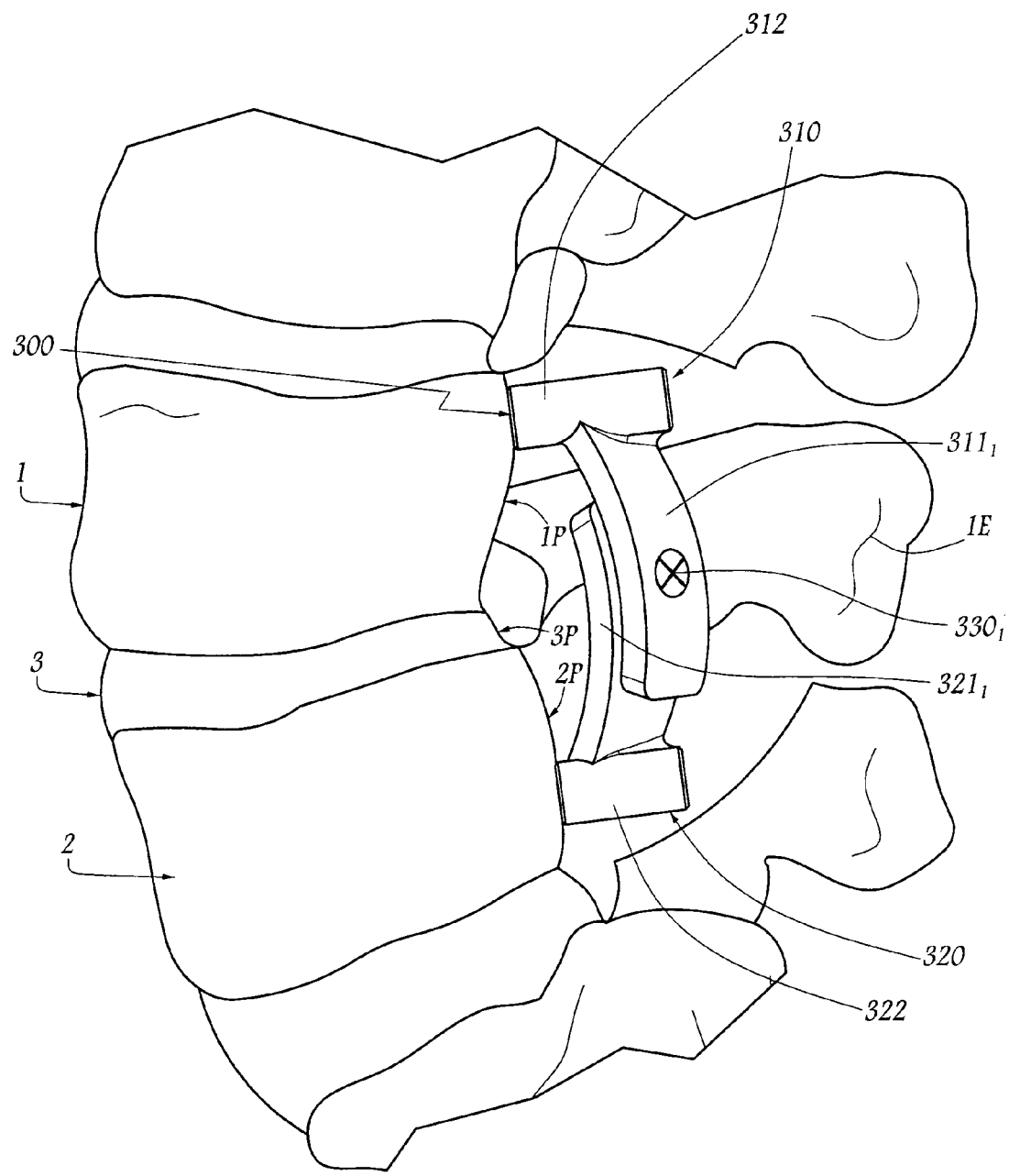
FIGS. 9 and 10 are views similar to FIGS. 1 and 2, illustrating the second embodiment of the device.
Figure 10:
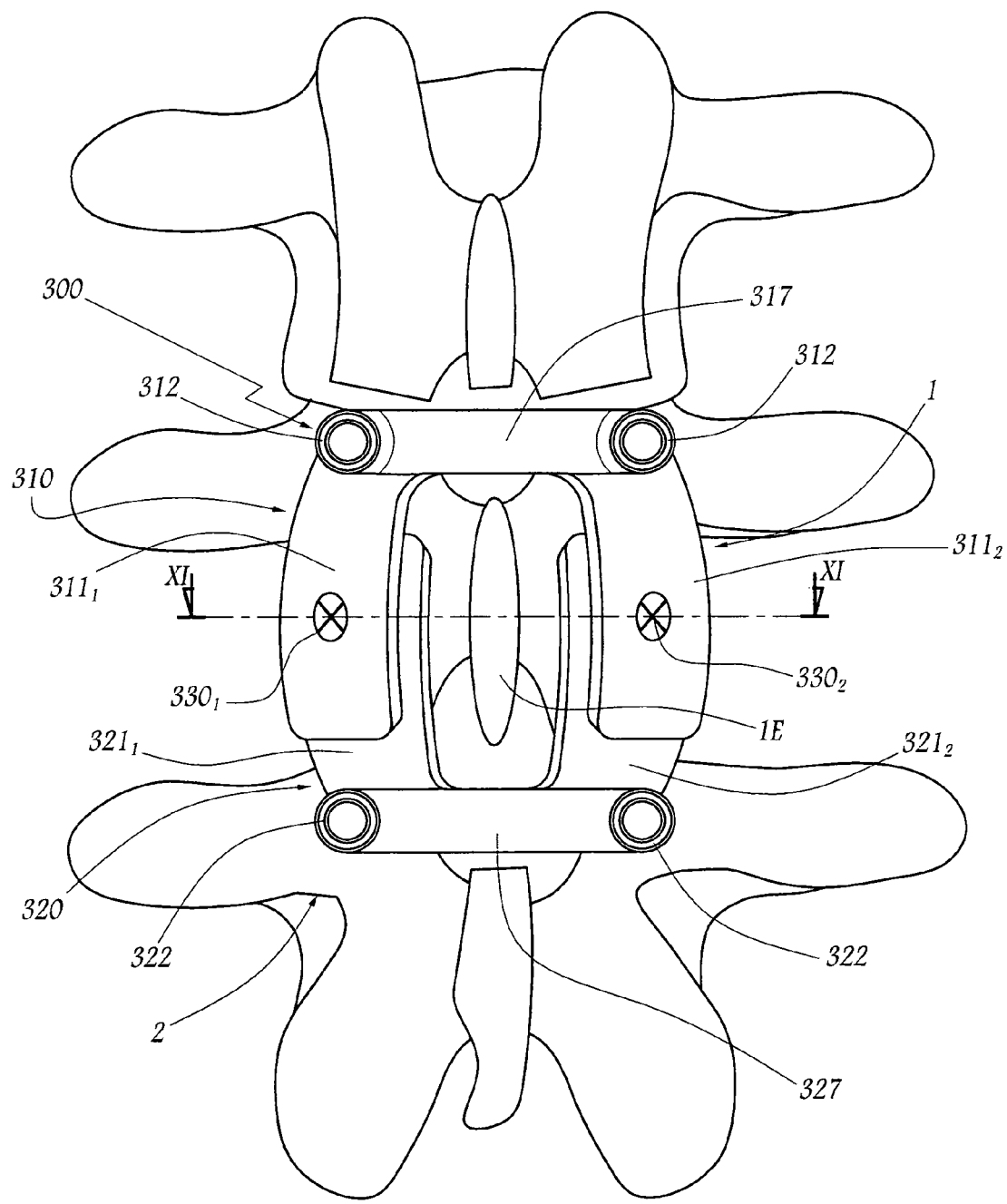

To allow the units 310 and 320 to be articulated to one another in a similar way to the units 210 and 220 of the device 200, each cup $311_1$ $311_2$, $321_1$, $321_2$ has a concave face facing toward the posterior side of the vertebrae 1 and 2 so that the anterior spherical surface $311_1$A, $311_2$A of each of the cups $311_1$ and $311_2$ covers in a complementary manner the posterior spherical surface $321_1$P, $321_2$P of one of the two cups $321_1$ and $321_2$, all these spherical surfaces $311_1$A, $311_2$A, $321_1$P and $321_2$P being centered at one and the same geometric point C located in the intervertebral space separating the vertebrae 1 and 2 as is clearly visible in FIG. 11. The point C corresponds to the center of the geometric sphere of which the surfaces $311_1$A, $311_2$A, $321_1$P and $321_2$P are portions in the form of surface quarters. Thus, the two surfaces $311_1$A, $311_2$A when considered together, each form half of an articulation surface that is functionally analogous to the anterior surface 121A of the unit 120 with respect to the articulation surface of which the surfaces $321_1$P and $321_2$P each form half, and which is functionally analogous to the posterior surface 111P of the unit 110.

Furthermore, the device 300 comprises dynamic limitation mechanical means 330, functionally analogous with the means 130. These means 330 consist of two parts associated respectively with the pairs of cups $311_1$ and $321_1$ and $311_2$, and $321_2$ in order respectively to limit the amplitude of sliding of the surfaces $311_1$A and $321_1$P, and $311_2$A, $321_2$P. For convenience, the structure of the parts $330_1$ and $330_2$ is not depicted in detail in FIGS. 8 to 11, each of these parts $330_1$ and $330_2$ being indicated only schematically in the form of a region marked with a cross in these figures. According to one practical embodiment, each part $330_1$, $330_2$ has the same structure as the means 130, including in particular pieces analogous to the pieces 131 and 132.

It will be noted that, because of the rigid connection afforded by the beams 317 and 327, one alternative form that has not been depicted might consist in providing just one of the parts $330_1$ and $330_2$. However, having both parts $330_1$ and $330_2$ present makes it possible to limit the amplitude of the relative movements of the units 310 and 320 uniformly in all conceivable directions in which they are called upon to move, particularly when the vertebrae 1 and 2 are caused to bend to the left/right.

The device 300 is implanted in a similar way to the device 100, in particular using one or two forks functionally analogous to the fork 140 and capable respectively of immobilizing the cups $311_1$ and $321_1$ and $311_2$ and $321_2$ with respect to one another.

Figure 12:
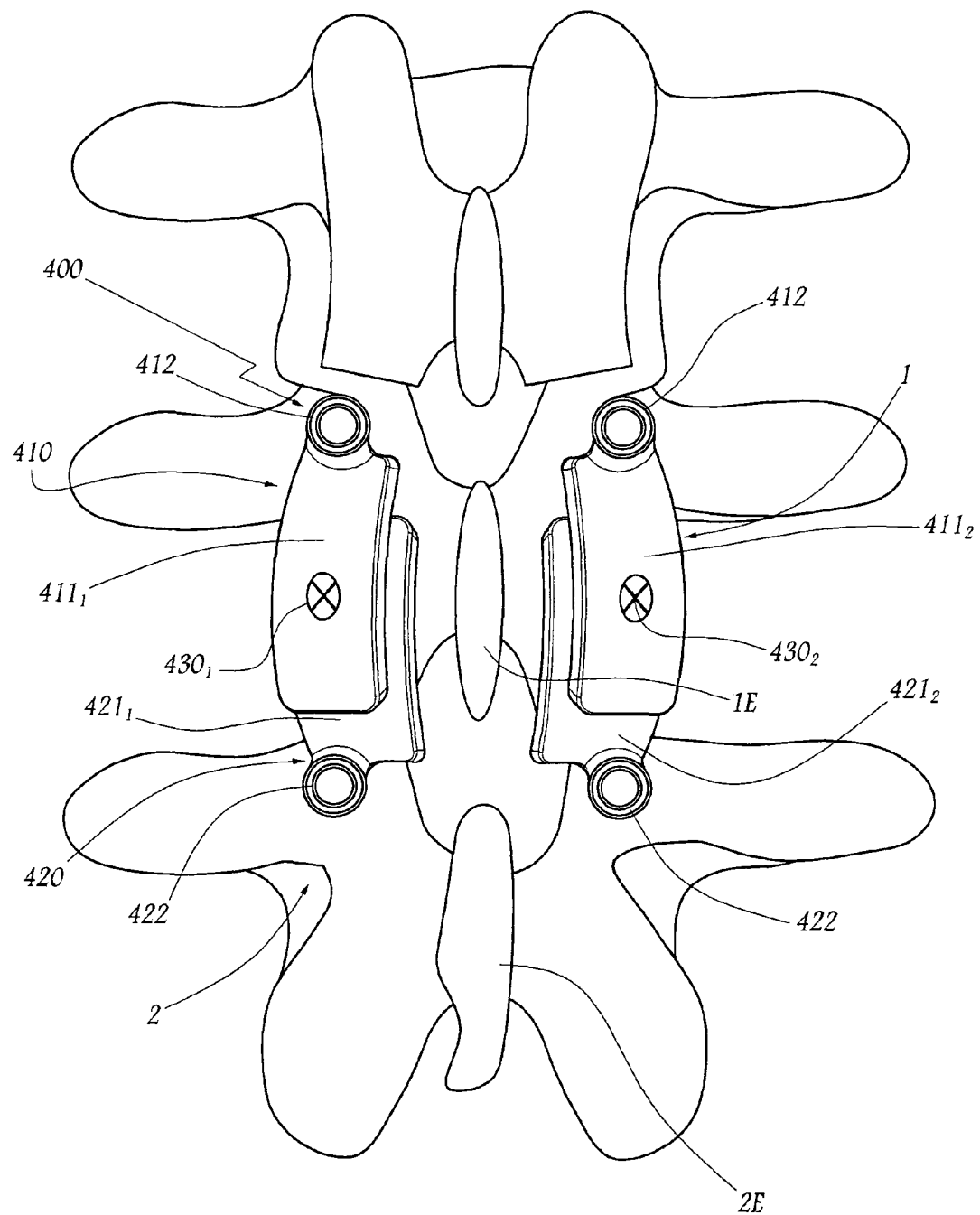
FIG. 12 is a view similar to FIG. 10, illustrating an alternative form of the second embodiment according to the invention.

FIG. 12 depicts an alternative form 400 of the device 300 which differs from the device 300 only in the lack of main section $317_1$ $327_1$ of the beams 317 and 327. Thus, the device 400 comprises a superior vertebral unit 410 and an inferior vertebral unit 420, the two respective cups $321_1$ and $321_2$, $421_1$ and $421_2$ of which are mechanically independent of one another in as much as they are not connected to one another in service by component parts of the device 400. The device 400 can thus be implanted without the need for any resection of the spinal processes 1E and 2E of the vertebrae 1 and 2 or of the spinal processes of the vertebra immediately adjacent thereto.

The device 400 further comprises mechanical means 430 capable of limiting the amplitude of the relative sliding of each pair of associated cups $411_1$ and $421_1$ and $411_2$ and $421_2$, respectively, these means being in the form of two parts $430_1$ and $430_2$ analogous to the parts $330_1$ and $330_2$ of the means 330 of the device 300.

The device 400 can be implanted in substantially the same way as the device 300, preferably using two forks to immobilize the cups $411_1$ and $421_1$, and $411_2$ and $421_2$ relative to one another, of the same type as the fork 140.

Various other arrangements and variations on the devices 100, 200, 300 and 400 described hereinabove are also conceivable. By way of example:

considering, for example the device 100, the overlapping structure of the cups 111 and 121 may be reversed so that, in an alternative form that has not been depicted, the cup of the superior vertebral unit 110 posteriorly covers the cup 121 of the inferior vertebral unit 120; such reversal of the overlapping structure of the two vertebral units have incidentally been illustrated in respect of the devices 300 and 400 considered hereinabove; and/or forms of embodiment other than those considered in the figures may be envisioned for the dynamic limitation means 130, 230, 330 and 430; in particular, if the idea of these limitation means being distributed one on each side, in an anterior-posterior direction, of the cups that are articulated to one another in terms of sliding is abandoned, then a peg functionally analogous to the peg 135 may be formed directly as an integral part of one of the two cups and housed, with clearance for travel, in an orifice functionally analogous to the orifice 115 and formed by the other cup, with provision for a washer and an assembly nut to be attached around the free end of this peg.

Figure 13:
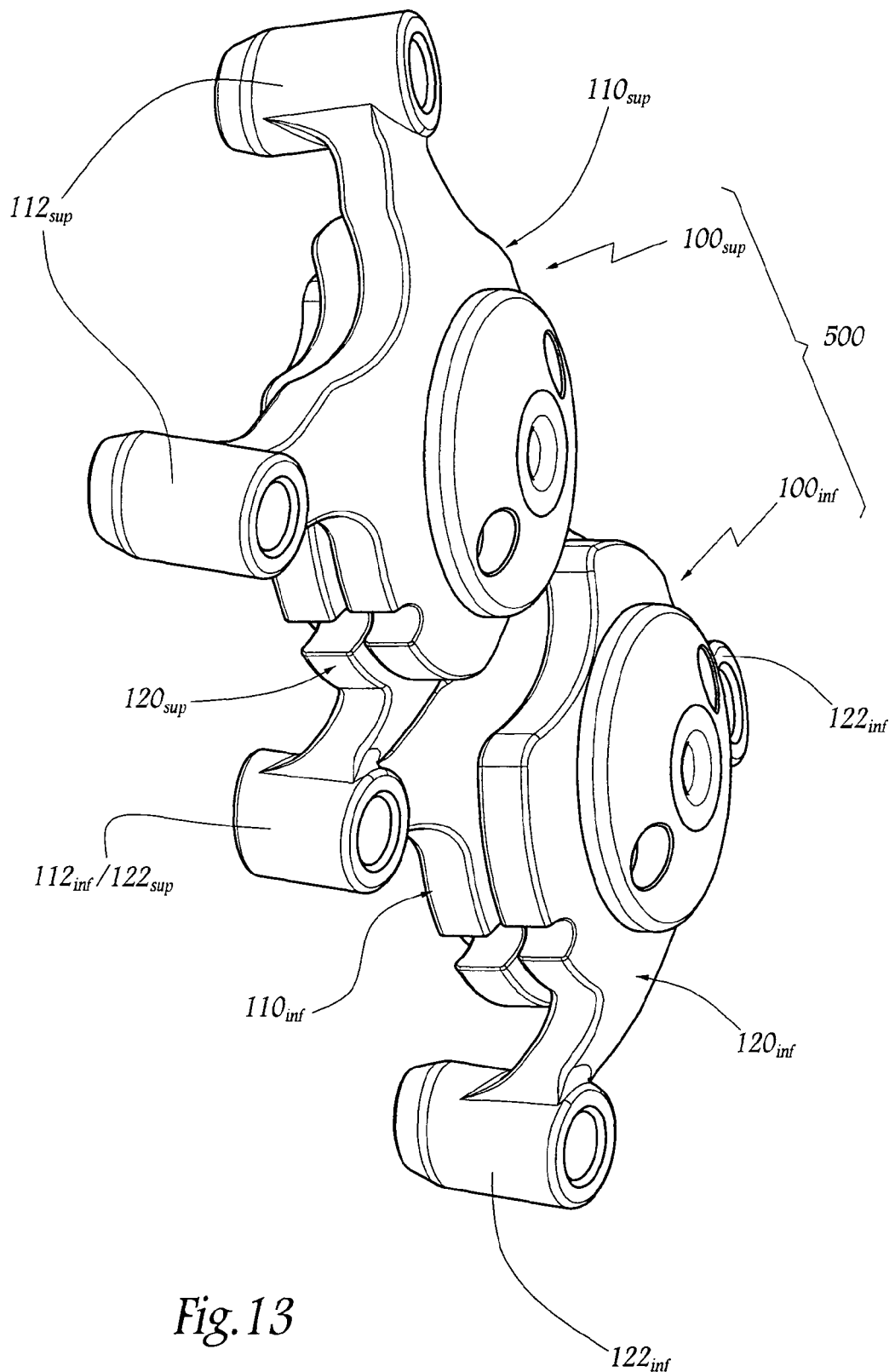
FIG. 13 is a perspective view of a guidance unit according to the invention.
Figure 14:
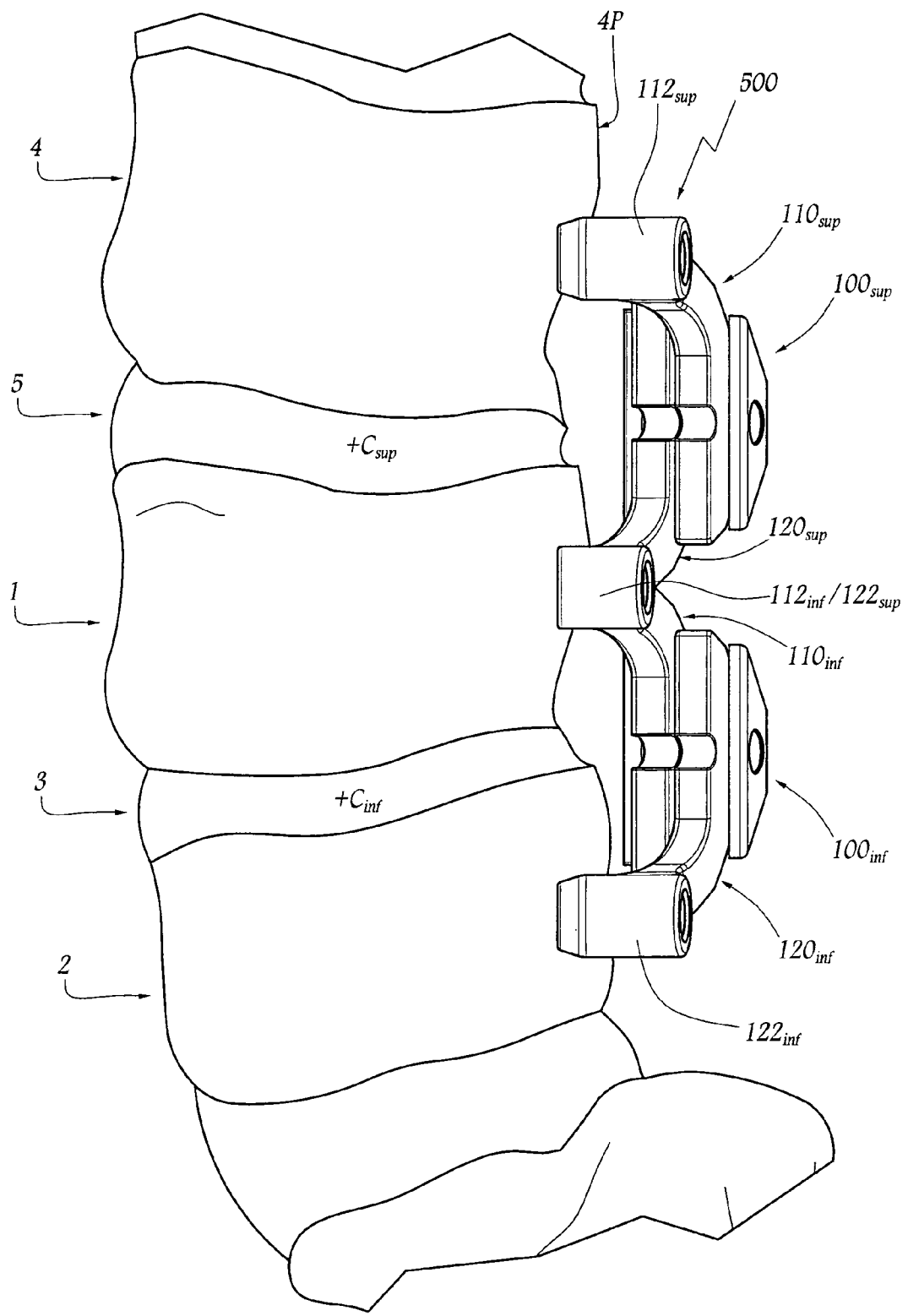
FIG. 14 is a view similar to FIG. 1 illustrating the unit of FIG. 13 in a configuration for implanting in a spine.

FIGS. 13 and 14 depict a unit 500 for guiding three adjacent vertebrae. This unit 500 for this purpose comprises two devices analogous to the device 100 of FIGS. 1 to 5, namely an inferior device $100_{inf}$ and a superior device $100_{sup}$. The device $100_{inf}$ is identical to the device 100 illustrated in FIGS. 1 to 5, and is depicted, in FIG. 14, implanted on the posterior side of the vertebrae 1 and 2. This device $100_{inf}$ thus comprises a superior vertebral unit $110_{inf}$ and inferior vertebral unit $120_{inf}$ these being respectively identical to the units 110 and 120 and implanted on the vertebrae 1 and 2 respectively using fixing pads $112_{inf}$ and $122_{inf}$ that are respectively identical to the pads 112 and 122.

The device $100_{sup}$ for its part has a structure analogous to that of the device 100 but reversed in as much as its superior vertebral unit $110_{sup}$ is positioned posterior to its inferior vertebral unit $120_{sup}$. The vertebral unit $110_{sup}$ is implanted on a vertebra 4 adjacent to the vertebra 1, but, on the opposite side to the vertebra 2, being situated above this vertebra 1, and separated therefrom by an intervertebral disk 5. For this, the vertebral unit $110_{sup}$ comprises two bone fastening pads $112_{sup}$ analogous to the pads 112 in as much as they internally delimit through-orifices for accepting a bone anchoring screw and which open onto the posterior face 4P of the vertebra 4.

The inferior vertebral unit $120_{sup}$ is implanted on the vertebra 1, via bone fixing pads $122_{sup}$ analogous to the pads 122. However, as is clearly visible in FIGS. 13 and 14, these pads $122_{sup}$ correspond to the pad $112_{inf}$ that is to say consist of the same components. In other words, the devices $100_{inf}$ and $100_{sup}$ are not independent of one another but are partially common because their pads $112_{inf}/122_{sup}$ for attachment to the vertebra 1 are the same.

Thus, the guide unit 500 occupies less space than the juxtaposition of two mechanically independent guide devices. Furthermore, the centers of articulation $C_{inf}$ and $C_{sup}$ associated respectively with the devices $100_{inf}$ and $100_{sup}$ are positioned relative to one another in a fixed and predetermined manner thus providing control over all of the dynamics imposed on the vertebral units $110_{inf}$, $120_{inf}$, $110_{sup}$ and $120_{sup}$ through the collaboration of their articulation surface centered on these centers. The extent to which the load on the disks 3 and 5 is relieved can therefore be controlled effectively, and in particular in a manner that is uniform across these two disks.

By way of alternative forms, not depicted, of the unit 500, one and/or other of its two devices $100_{inf}$ and $100_{sup}$ can be produced in the form of the devices 200, 300 and 400. Likewise, more than two guidance devices of the type of those 100, 200, 300 and 400 may be incorporated into one and the same guide unit of the type of the unit 500, in order to treat four or more adjacent vertebrae.

The invention claimed is:

1. A device for posterior dynamic guidance of the spine, comprising two vertebral units respectively designed to be fixed to the posterior side of two adjacent vertebrae of the spine, wherein each of the two vertebral units respectively define complementary articulation surfaces in the form of semi-spherical cups which, when the two vertebral units are fixed to the vertebrae with one cup positioned over the other, extend overall on the posterior side of the vertebrae and on each side of a saggital plane of the vertebrae and slide one within the another, the cups being centered at one geometric point, which when implanted is located in the intervertebral space that separates the two vertebrae, and wherein the device includes mechanical means to limit a degree of the relative sliding of the two cups relative to one another.

2. The device according to claim 1, wherein the single cup of each vertebral unit has a concave face facing toward the posterior side of an associated vertebra when the vertebral unit is fixed to the associated vertebra.

3. The device according to claim 1, wherein each vertebral unit includes two pads for fixing to the posterior face of the vertebra associated with the unit when implanted, which pads are spaced from one another in a substantially medio-lateral direction and are both connected to respective ears extending from each cup and with each ear forming a peripheral extension with the same curvature of the cup from which it extends.

4. The device according to claim 1, wherein each unit includes two pads for bone fixing to the posterior face of the vertebra associated with the unit, which pads are spaced from one another in a substantially medio-lateral direction when implanted and are joined together by a reinforcing beam both equipped with the pads at each of its longitudinal ends and connected rigidly to one of the cups.

5. The device according to claim 1, wherein the mechanical means includes, firstly, a peg connected to a first of the two vertebral units and at least partially extending from the the cap of the first vertebral unit toward the cap of a second of the two vertebral units and, secondly, an orifice that houses the peg with clearance, this orifice being formed by the second vertebral unit and opening onto the cap of the second vertebral unit.

6. The device according to claim 5, wherein the orifice passes hrough the second vertebral unit in a substantially anterior-posterior direction when implanted and thus opens onto surface of the cap of the second vertebral unit a concave surface of the second vertebral unit, and wherein the peg extends into this orifice, fixedly connecting first and second assembly pieces positioned on opposite sides of the caps of the first and second vertebral units.

7. The device according to claim 6, wherein the concave surface of the second vertebral unit is spherical such as to be concentric with the articulation surfaces, and wherein the first assembly piece has a semi-spherical surface that complements the concave surface and is designed to slide against the concave surface during relative sliding of the caps of the first and second vertebral units.

8. The device according to claim 1, wherein the device further includes an elastic shock-absorbing means interposed between the two vertebral units.

9. A unit for the posterior dynamic guidance of the spine, wherein the unit comprises at least two devices according to claim 1, and wherein a first vertebral unit of one of the devices and a first vertebral unit of another of the devices are joined to one another at a bone attachment area and are designed to be fixed to a common intermediate vertebra while the second vertebral units of the two devices are respectively designed to be fixed to an inferior vertebra and a superior vertebra which are adjacent to the intermediate vertebra.

10. A system for treating the spine, wherein the system comprises a device according to claim 1 and an immobilizing means for temporarily immobilizing the device, which is designed to be removably connected to the two vertebral units and therefore prevent relative sliding of the articulation surfaces.

11. The system according to claim 10, wherein the immobilizing means includes two pins housed respectively in complementary notches formed in the vertebral units, the two notches of each vertebral unit being both aligned in a direction passing through a central region of the caps and on opposite sides of the caps.

12. A device for posterior dynamic guidance of the spine, comprising two vertebral units respectively designed to be fixed to the posterior side of two adjacent vertebrae of the spine, wherein each of the two vertebral units respectively define substantially spherical complementary articulation surfaces in the form of a pair of two separate semi-spherical cups which are spaced from one another in a substantially medio-lateral direction when implanted and each delimiting approximately half of the corresponding articulation surfaces, the two cups of one of the two vertebral units being mounted over the two cups of the other of the two vertebral units when implanted and which, when the two vertebral units are fixed to the vertebrae, extend overall on the posterior side of the vertebrae and slide relative to one another, all the semi-spherical cups having concave surfaces which are centered at a common geometric point located in an intervertebral space separating the two adjacent vertebrae when implanted and, wherein the device also includes a mechanical means to limit a degree of the relative sliding of the cups relative to one another.

13. The device according to claim 12, wherein each cup of said pair of each vertebral unit has a concave face facing toward the posterior side of the associated vertebra when the vertebral unit is fixed to the associated vertebra.

14. The device according to claim 12, wherein each vertebral unit includes two pads for fixing to the posterior face of the vertebra associated with the unit, which pads are spaced from one another in a substantially medio-lateral direction when implanted and are both connected to each cup of said pair by respective ears each forming a peripheral extension of each cup with the same curvature.

15. The device according to claim 12, wherein each unit includes two pads for bone fixing to the posterior face of the vertebra associated with the unit when implanted, which pads are from one another in a substantially medio-lateral direction and are joined together by a reinforcing beam both equipped with the pads at each of its longitudinal ends and connected rigidly to each of the two cups of each unit cup.

* * * * *